(12) United States Patent
Zhang et al.

(10) Patent No.: US 11,564,966 B2
(45) Date of Patent: Jan. 31, 2023

(54) METHOD FOR SEPARATING EIGHT COMPONENTS IN CHINESE TRADITIONAL MEDICINE COMPOSITION

(71) Applicant: Shijiazhuang Yiling Pharmaceutical Co., Ltd., Shijiazhuang (CN)

(72) Inventors: Chuangfeng Zhang, Shijiazhuang (CN); Shuo Shen, Shijiazhuang (CN); Lianqiang Song, Shijiazhuang (CN)

(73) Assignee: Shijiazhuang Yiling Pharmaceutical Co., Ltd., Shijiazhuang (CN)

( * ) Notice: Subject to any disclaimer, the term of this patent is extended or adjusted under 35 U.S.C. 154(b) by 298 days.

(21) Appl. No.: 16/761,780

(22) PCT Filed: Oct. 25, 2018

(86) PCT No.: PCT/CN2018/111846
§ 371 (c)(1),
(2) Date: May 5, 2020

(87) PCT Pub. No.: WO2019/091287
PCT Pub. Date: May 16, 2019

(65) Prior Publication Data
US 2020/0390840 A1    Dec. 17, 2020

(30) Foreign Application Priority Data
Nov. 10, 2017    (CN) .......................... 201711103420.2

(51) Int. Cl.
| | |
|---|---|
| *A61K 36/634* | (2006.01) |
| *A61K 31/05* | (2006.01) |
| *A61K 33/06* | (2006.01) |
| *A61K 36/11* | (2006.01) |
| *A61K 36/17* | (2006.01) |
| *A61K 36/315* | (2006.01) |
| *A61K 36/41* | (2006.01) |
| *A61K 36/484* | (2006.01) |
| *A61K 36/53* | (2006.01) |
| *A61K 36/708* | (2006.01) |
| *A61K 36/736* | (2006.01) |
| *A61K 36/78* | (2006.01) |

(52) U.S. Cl.
CPC ............ *A61K 36/634* (2013.01); *A61K 31/05* (2013.01); *A61K 33/06* (2013.01); *A61K 36/11* (2013.01); *A61K 36/17* (2013.01); *A61K 36/315* (2013.01); *A61K 36/41* (2013.01); *A61K 36/484* (2013.01); *A61K 36/53* (2013.01); *A61K 36/708* (2013.01); *A61K 36/736* (2013.01); *A61K 36/78* (2013.01); *A61K 2236/13* (2013.01); *A61K 2236/15* (2013.01); *A61K 2236/333* (2013.01); *A61K 2236/39* (2013.01)

(58) Field of Classification Search
None
See application file for complete search history.

(56) References Cited

FOREIGN PATENT DOCUMENTS

| | | |
|---|---|---|
| CN | 1970000 A | 5/2007 |
| CN | 102040641 A | 5/2011 |
| CN | 102040641 B | 10/2014 |
| WO | 2017148418 A1 | 9/2017 |
| WO | 2017148426 A1 | 9/2017 |

*Primary Examiner* — Susan Hoffman
(74) *Attorney, Agent, or Firm* — Leason Ellis LLP

(57) ABSTRACT

The solution provides a method for separating a Chinese traditional medicine composition. To explain a pharmacological effect mechanism of a medicine made of two or more components and scientific content in rules of compatibility among components of a compound medicine, systematic researches on the material basis is very necessary. Accordingly, deep researches are done on chemical components of the pharmaceutical composition in the solution, and eight compounds are separated, which are 10-O-(p-hydroxycinnamoyl)-adoxosidic acid, aloe-emodin-8-O-β-D-glucopyranoside, quercitrin, matairesinol-4'-O-glucoside, liquiritin apioside, epi-vogeloside, vogeloside and ethyl caffeate, which provides a new quality control method for the composition in the solution.

10 Claims, 2 Drawing Sheets

US 11,564,966 B2

METHOD FOR SEPARATING EIGHT COMPONENTS IN CHINESE TRADITIONAL MEDICINE COMPOSITION

CROSS-REFERENCE TO RELATED APPLICATIONS

This application is a national stage application of International Application No. PCT/CN2018/111846, filed on Oct. 25, 2018, which claims priority to Chinese Patent Application No. CN201711103420.2, filed on Nov. 10, 2017. The disclosures of the aforementioned applications are hereby incorporated herein by reference in their entireties.

TECHNICAL FIELD

The disclosure relates to a method for separating multiple components in a Chinese traditional medicine composition.

BACKGROUND

The Chinese traditional medicine compound prescription is the main form of Chinese traditional medicine, after thousands of years of clinical use, the compound prescription can obtain a stronger therapeutic effect than a single medicine, which has fully proved the scientific nature of the compound prescription. The medicinal composition of the solution is composed of 13 Chinese traditional medicines such as fructus Forsythiae, honeysuckle, herbaephedrae (processed) and the like, has the effects of clearing heat and detoxifying, removing lung hotness, and is used for treating epidemic influenza. Clinical studies prove that the medicinal composition of the solution has definite therapeutic effect and remarkable effect on treating influenza and acute upper respiratory tract infection. To explain a pharmacological effect mechanism of a medicine made of two or more components and scientific content in rules of compatibility among components of a compound medicine, systematic researches on the material basis is very necessary. Accordingly, deep researches are done on chemical components of the pharmaceutical composition in the solution, and eight compounds are separated, which are 10-O-(p-hydroxycinnamoyl)-adoxosidic acid, aloe-emodin-8-O-β-D-glucopyranoside, quercitrin, matairesinol-4'-O-glucoside, liquiritin apioside, epi-vogeloside, vogeloside and ethyl caffeate, which provides a new quality control method for the composition in the solution.

SUMMARY

These and other problems are generally solved or circumvented, and technical advantages are generally achieved, by embodiments of the present disclosure which provide method for separating eight components in Chinese traditional medicine composition.

The solution provides a method for separating eight compounds in a Chinese traditional medicine composition.

The Chinese traditional medicine composition is prepared from the following raw materials in parts by weight: 200-300 parts of fructus Forsythiae, 60-100 parts of ephedra, 40-60 parts of *Rheum officinale,* 200-300 parts of *Houttuyni acordata,* 200-300 parts of honeysuckle, 200-300 parts of isatis root, 60-100 parts of *Pogostemon cablin,* 200-300 parts of *Rhizoma dryopteris* crassirhizomatis, 60-100 parts of *Rhodiola rosea,* 5-9 parts of menthol, 60-100 parts of semen *Armeniacae amarum,* 60-100 parts of liquorice and 200-300 parts of *Gypsum fibrosum.*

An embodiment separation method in the solution comprises the following steps of:

(1) adsorbing the total extract of the Chinese traditional medicine composition by macroporous resin AB-8™, eluting with water, 10% ethanol, 30% ethanol and 50% ethanol in sequence, respectively collecting eluent of each part, and concentrating to obtain extract of each part;

(2) taking the 50% ethanol elution part extract obtained in step (i), adding reverse-phase silica gel ODS-AQ-HG™, naturally airing the mixed sample, loading the sample, separating by using a reverse-phase ODS-AQ-HG™ open column, and sequentially eluting by using methanol with methanol-water volume ratios of 20:80, 40:60, 60:40, 80:20 and 100% methanol; sequentially obtaining Fr.A-Fr.E;

(3) taking Fr.A sample obtained in step (2), adding a reverse-phase silica gel ODS-AQ-HG™ to mix sample, naturally airing the mixed sample ODS, adding the mixed sample ODS into a sample loading column, separating liquid phase prepared by an upper medium-pressure, gradiently separating liquid phase prepared by medium-pressure, wherein the volume ratio of methanol to water is 25:75-60:40, and the flow rate is 25 mL/min, receiving the fractions in equal volume of 500 mL in a conical flask, concentrating under reduced pressure, identifying the combined fractions through a thin layer chromatography plate, and concentrating under reduced pressure again to obtain Fr.A-1-Fr.A-7;

(4) mixing the Fr.A-2 sample obtained in the step (3) with silica gel, loading onto a silica gel column, carrying out isocratic separation by using a dichloromethane-methanol volume ratio of 8:1, receiving fractions in equal volume of 50 mL, eluting with a volume of 800 mL, and identifying the combined fractions through thin-layer chromatography plate to obtain Fr.A-2-1-Fr.A-2-4;

(5) dissolving the Fr.A-2-2 sample obtained in the step (4) with methanol, adopting high performance liquid chromatography, wherein the volume ratio of methanol to water in the mobile phase is 50:50, the flow rate is 12 mL/min, and detection wavelength is 210 nm, to perform primary separation and respectively collecting chromatographic peaks with retention times of 6-8 min, 9-10 min and 12-13 min, recovering the solvent under reduced pressure, and respectively performing the following separation:

a chromatographic peak of 6-8 min, further purified by high performance liquid chromatography, wherein the volume ratio of acetonitrile to water in the mobile phase is 25:75, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 8-9 min, recovering the solvent under decompression to obtained compound 2: aloe-emodin-8-O-β-D-glucopyranoside;

a chromatographic peak of 9-10 min, further purified by high performance liquid chromatography, wherein the volume ratio of methanol to water in the mobile phase is 45:55, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 21-23 min, recovering the solvent under decompression to obtained compound 3: quercitrin;

a chromatographic peak of 12-13 min, further purified by high performance liquid chromatography, wherein the volume ratio of acetonitrile to water in the mobile phase is 25:75, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 9-10 min, recovering the solvent under decompression to obtained compound 4: matairesinol-4'-O-glucoside;

(6) dissolving the Fr.A-2-3 sample obtained in the step (4) with methanol, adopting high performance liquid chromatography, wherein the volume ratio of methanol to water in the mobile phase is 30:70, the flow rate is 12 mL/min, and detection wavelength is 210 nm, to perform primary separation and respectively collecting chromatographic peaks with retention times of 10-11 min, 17-19 min and 21-24 min, recovering the solvent under reduced pressure, chromatographic peaks of 17-19 min is for compound 6: epi-vogeloside, chromatographic peaks of 21-24 min is for compound 7: vogeloside, a chromatographic peak of 10-11 min, further purified by high performance liquid chromatography, wherein the volume ratio of acetonitrile to water in the mobile phase is 15:85, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 14-16 min, recovering the solvent under decompression to obtained compound 5: liquiritin apioside; and (7) dissolving the Fr.A-3 sample obtained in the step (3) with methanol, adopting high performance liquid chromatography, wherein the volume ratio of methanol to water in the mobile phase is 60:40, the flow rate is 12 mL/min, and detection wavelength is 210 nm, to perform primary separation and respectively collecting chromatographic peaks with retention times of 14-15 min and 19-21 min, and recovering the solvent under reduced pressure, separating out a white precipitate in a dichloromethane-methanol solution with volume ratio of 2:1 from a collecting liquid of chromatographic peak of 19-21 min to obtain a compound 8; a chromatographic peak of 14-15 min, further purified by high performance liquid chromatography, wherein the volume ratio of acetonitrile to water in the mobile phase is 30:70, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 18-20 min, recovering the solvent under decompression to obtained compound 1: 10-O-(p-hydroxycinnamoyl)-adoxosidic acid.

An embodiment separation method in the solution comprises the following steps of:

(1) adsorbing 5 kg the total extract of the Chinese traditional medicine composition by macroporous resin AB-8™, eluting with 150 L water, 87.5 L 10% ethanol, 225 L 30% ethanol and 250 L 50% ethanol in sequence, and concentrating to obtain extract of each part;

(2) taking 200 g the 50% ethanol elution part extract obtained in the step (1), adding 200 g reversed-phase silica gel ODS-AQ-HG™ S-50 μm to mix sample, naturally airing the mixed sample ODS, loading the sample, and separating by using a reversed-phase ODS-AQ-HG™ S-50 μm open column, wherein the sample height ratio is 1:4; eluting with 6 L methanol-water in a volume ratio of 20:80, 7 L in a volume ratio 40:60, 7 L in a volume ratio 60:40, 5 L in a volume ratio 80:20 and 3 L 100% methanol in sequence under reduced pressure to obtain Fr.A-Fr.E;

(3) taking 50.0 g Fr.A sample obtained in step (2), adding 50 g reverse-phase silica gel ODS-AQ-HG™ S-50 μm to mix sample, naturally airing the mixed sample ODS, adding the mixed sample ODS into a sample loading column, separating liquid phase prepared by an upper medium-pressure, wherein a separating column filler is reversed-phase silica gel ODS-AQ-HG™ S-50 μm, gradiently separating liquid phase prepared by medium-pressure, wherein the volume ratio of methanol to water is 25:75-60:40, and the flow rate is 25 mL/min, receiving the fractions in equal volume of 500 mL in a conical flask, concentrating under reduced pressure, identifying the combined fractions through a thin layer chromatography plate, and concentrating under reduced pressure again to obtain Fr.A-1-Fr.A-7;

(4) mixing 3.2 g Fr.A-2 sample obtained in the step (3) with 6.4 g silica gel of 200-300 mesh, loading onto a silica gel column, wherein the sample height ratio is 1:50, carrying out isocratic separation by using a dichloromethane-methanol volume ratio of 8:1, receiving fractions in equal volume of 50 mL, eluting with a volume of 800 mL, and identifying the combined fractions through thin-layer chromatography plate to obtain Fr.A-2-1-Fr.A-2-4;

(5) dissolving the Fr.A-2-2 sample obtained in the step (4) with methanol, the solution is filtered through a 0.45 μm microporous membrane, adopting high performance liquid chromatography, wherein the volume ratio of methanol to water in the mobile phase is 50:50, the flow rate is 12 mL/min, and detection wavelength is 210 nm, to perform primary separation and respectively collecting chromatographic peaks with retention times of 6-8 min, 9-10 min and 12-13 min, recovering the solvent under reduced pressure, and respectively performing the following separation:

the chromatographic peak of 6-8 min, further purified by high performance liquid chromatography, wherein the volume ratio of acetonitrile to water in the mobile phase is 25:75, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 8-9 min, recovering the solvent under decompression to obtained compound 2: aloe-emodin-8-O-β-D-glucopyranoside;

the chromatographic peak of 9-10 min, further purified by high performance liquid chromatography, wherein the volume ratio of methanol to water in the mobile phase is 45:55, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 21-23 min, recovering the solvent under decompression to obtained compound 3: quercitrin;

the chromatographic peak of 12-13 min, further purified by high performance liquid chromatography, wherein acetonitrile to water in the mobile phase is 25:75, the flow rate is 12 mL/min, and the detection wavelength is 210 nm, chromatographic column liquid chromatographic column YMC-Pack R&D ODS-A™, 250×20 mm, S-10 μm, under these conditions, collecting the chromatographic peak with retention times of 9-10 min, recovering the solvent under decompression to obtained compound 4: matairesinol-4'-O-glucoside;

(6) dissolving the Fr.A-2-3 sample obtained in the step (4) with methanol, the solution is filtered through a 0.45 μm microporous membrane, adopting high performance liquid chromatography, wherein the volume ratio of methanol to water in the mobile phase is 30:70, the flow rate 1512 mL/min, and detection wavelength is 210 nm, to perform primary separation and respectively collecting chromatographic peaks with retention times of 10-11 min, 17-19 min and 21-24 min, recovering the solvent under reduced pressure, chromatographic peaks of 17-19 min is for compound 6: epi-vogeloside, chromatographic peaks of 21-24 min is for compound 7: vogeloside, a chromatographic peak of 10-11 min, further purified by high performance liquid chromatography, wherein the volume ratio of acetonitrile to water in the mobile phase is 15:85, the flow rate is 12 mL/min, and the detection wavelength is 210 nm, chromatographic column: liquid chromatographic column YMC-Pack R&D ODS-ATM, 250×20 mm, S-10 μm, under these conditions, collecting the chromatographic peak with retention times of 14-16 min, recovering the solvent under decompression to obtained compound 5: liquiritin apioside; and (7) dissolving the Fr.A-2-3 sample obtained in the step (3) with methanol, the solution is filtered through a 0.45 μm microporous membrane, adopting high performance liquid chromatography, wherein the volume ratio of methanol to water in the mobile phase is 60:40, the flow rate is 12 mL/min, and detection wavelength is 210 nm, to perform primary separation and respectively collecting chromatographic peaks with retention times of 14-15 min and 19-21 min, and recovering the solvent under reduced pressure, separating out a white precipitate in a dichloromethane-methanol solution with volume ratio of 2:1 from a collecting liquid of chromatographic peak of 19-21 min to obtain a compound 8; a chromatographic peak of 14-15 min, further purified by high performance liquid chromatography, wherein the volume ratio of acetonitrile to water in the mobile phase is 30:70, the flow rate is 12 mL/min, and the detection wavelength is 210 nm, chromatographic column: liquid chromatographic column YMC-Pack R&D ODS-A™, 250×20 mm, S-10 μm, under these conditions, collecting the chromatographic peak with retention times of 18-20 min, recovering the solvent under decompression to obtained compound 1: 10-O-(p-hydroxycinnamoye-adoxosidic acid.

In one embodiment, the Chinese traditional medicine composition is prepared from the following raw materials in parts by weight: 200 parts of fructus Forsythiae, 300 parts of honeysuckle, 200 parts of isatis root, 40 parts of *Rheum officinale*, 60 parts of *Pogostemon cablin*, 300 parts of *Rhizoma dryopteris* crassirhizomatis, 100 parts of *Rhodiola rosea*, 9 parts of menthol, 60 parts of ephedra, 100 parts of semen *Armeniacae amarum*, 200 parts of *Houttuyni acordata*, 100 parts of liquorice and 200 parts of *Gypsum fibrosum*.

In one embodiment, the Chinese traditional medicine composition is prepared from the following raw materials in parts by weight: 300 parts of fructus Forsythiae, 200 parts of honeysuckle, 300 parts of isatis root, 60 parts of *Rheum officinale*, 100 parts of *Pogostemon cablin*, 200 parts of *Rhizoma dryopteris* crassirhizomatis, 60 parts of *Rhodiola rosea*, 5 parts of menthol, 100 parts of ephedra, 60 parts of semen *Armeniacae amarum*, 300 parts of *Houttuyni acordata*, 60 parts of liquorice and 300 parts of *Gypsum fibrosum*.

In one embodiment, the Chinese traditional medicine composition is prepared from the following raw materials in parts by weight: 278 parts of fructus Forsythiae, 294 parts of honeysuckle, 285 parts of isatis root, 55 parts of *Rheum officinale*, 95 parts of *Pogostemon cablin*, 290 parts of *Rhizoma dryopteris* crassirhizomatis, 87 parts of *Rhodiola rosea*, 8.5 parts of menthol, 88 parts of ephedra, 80 parts of semen *Armeniacae amarum*, 284 parts of *Houttuyni acordata*, 95 parts of liquorice and 277 parts of *Gypsum fibrosum*.

The total extract of the Chinese traditional medicine composition in the scheme is prepared from the following steps of:

(1) weighing the Chinese traditional medicinal materials according to the weight ratio of the raw material medicines, cleaning and selecting, and crushing as appropriate;

(2) crushing *Pogostemon cablin*, adding 10 times of water to extract volatile oil, extracting for 8 hours, and collecting the volatile oil for later use; after filtering the extracting solution, discarding the residue, and taking the filtrate for later use;

(3) extracting fructus Forsythiae, ephedra, *Houttuyni acordata* and *Rheum officinale* three times with 12 times of 70% ethanol for 2.5 hours each time, combining and filtering the extracting solutions, recovering ethanol, and taking the filtrate for later use;

(4) honeysuckle, *Gypsum fibrosum*, isatis root, *Rhizoma dryopteris* crassirhizomatis, liquorice and *Rhodiola rosea*, adding 12 times of water for decocting to boil, adding semen *Armeniacae amarum*, decocting twice for 1 hour each time, combining and filtering the extracting solutions, combining the obtained filtrate with the filtrate after *Pogostemon cablin* oil extraction in the step (2), concentrating to a clear paste with a relative density of 1.10-1.15 measured at 60° C., adding ethanol to adjust the alcohol concentration to 70%, and refrigerating and standing; filtering and recovering ethanol until no alcohol smell exists to obtain clear paste for later use; and (5) combining the clear paste obtained in the step (4) with the alcohol extract obtained in the step (3), concentrating to a clear paste with a relative density of 1.15-1.20 measured at 60° C., and drying to obtain the total extract for later use.

Advantageous effects of the embodiments include at least the following. The embodiment separation method provided by the solution can separate and obtain eight compounds, namely 10-O-(p-hydroxycinnamoyl)-adoxosidic acid, aloe-emodin-8-O-β-D-glucopyranoside, quercitrin, matairesinol-4'-O-glucoside, liquiritin apioside, epi-vogeloside, vogeloside and ethyl caffeate.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the aft that such equivalent constructions do not depart from the spirit and scope of the disclosure as set forth in the appended claims.

DESCRIPTION OF THE DRAWINGS

For a more complete understanding of the present disclosure, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

Figure 1:
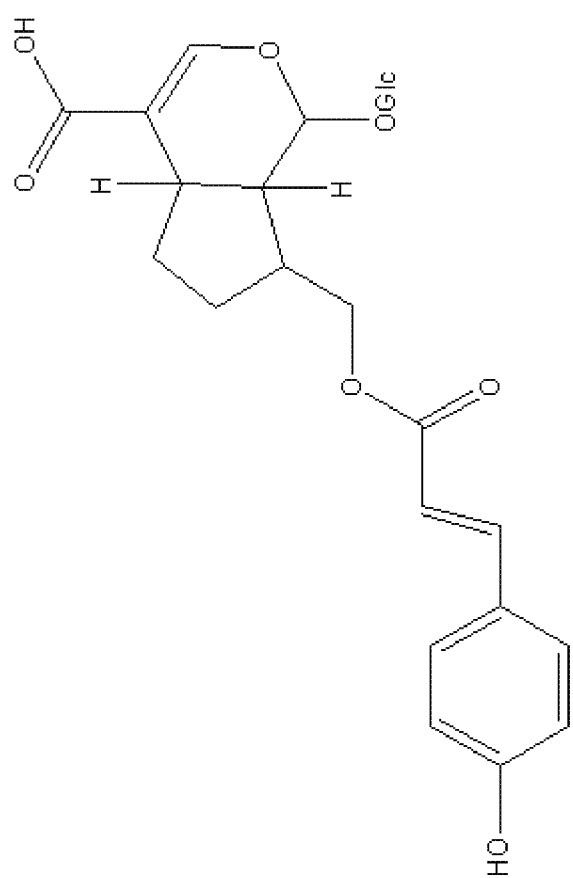
FIG. 1 is a diagram illustrating a molecular structure of an embodiment compound.

The making and using of the embodiments of this disclosure are discussed in detail below. It should be appreciated, however, that the concepts disclosed herein can be embodied in a wide variety of specific contexts. The specific embodiments discussed are merely illustrative, and do not limit the scope of the claims.

Example 1

An embodiment method includes weighing in proportion: 20 kg fructus Forsythiae, 30 kg honeysuckle, 20 kg isatis root, 4 kg *Rheum officinale,* 6 kg *Pogostemon cablin,* 30 kg *Rhizoma dryopteris* crassirhizomatis, 10 kg *Rhodiola rosea,* 0.9 kg menthol, 6 kg ephedra, 10 kg semen *Armeniacae amarum,* 20 kg *Houttuyni acordata,* 10 kg liquorice and 20 kg *Gypsum fibrosum,* and extracting according to the following processes:

(1) weighing the Chinese traditional medicinal materials according to the weight ratio of the raw material medicines, cleaning and selecting, and crushing as appropriate;

(2) crushing *Pogostemon cablin,* adding 10 times of water to extract volatile oil, extracting for 8 hours, and collecting the volatile oil for later use; after filtering the extracting solution, discarding the residue, and taking the filtrate for later use;

(3) extracting fructus Forsythiae, ephedra, *Houttuyni acordata* and *Rheum officinale* three times with 12 times of 70% ethanol for 2.5 hours each time, combining and filtering the extracting solutions, recovering ethanol, and taking the filtrate for later use;

(4) honeysuckle, *Gypsum fibrosum,* isatis root, *Rhizoma dryopteris* crassirhizomatis, liquorice and *Rhodiola rosea,* adding 12 times of water for decocting to boil, adding semen *Armeniacae amarum,* decocting twice for 1 hour each time, combining and filtering the extracting solutions, combining the obtained filtrate with the filtrate after *Pogostemon cablin* oil extraction in the step (2), concentrating to a clear paste with a relative density of 1.15 measured at 60° C., adding ethanol to adjust the alcohol concentration to 70%, and refrigerating and standing; filtering and recovering ethanol until no alcohol smell exists to obtain clear paste for later use; and (5) combining the clear paste obtained in the step (4) with the alcohol extract obtained in the step (3), concentrating to a clear paste with a relative density of 1.20 measured at 60° C., and drying to obtain the total extract for later use.

An embodiment separation method comprises the following steps.

1. Preparation of Instruments and Materials

What are to be prepared may include: Bruker Alpha infrared spectrometer (Bruker, Switzerland); Bruker AVIIIHD 600 nuclear magnetic resonance spectrometer (Bruker, Switzerland); Synapt G2-S Mass spectrometer (Waters, USA); Combi Flash Rf medium and low-pressure preparative liquid chromatograph (Teledyne ISCO, USA); NP7000 preparative liquid chromatograph (Jiangsu Hanbom Science and Technology Co., Ltd.) Milli-Q pure water purifier (Millipore, USA); AL204 analytical electronic balance (Mettler Toledo, USA); YMC ODS-AQ-HG 50 μm reverse phase silica gel (YMC Corporation, Japan); column chromatography silica gel (100-200 mesh and 200-300 mesh, Qingdao Haiyang Chemical CO., Ltd.); thin-layer chromatography silica gel plate $GF_{254}$ (Qingdao Haiyang Chemical CO., Ltd); YMC-Pack R&D ODS-A (250×20 mm, S-10 μm, YMC Corporation, Japan); total extract of the Chinese traditional medicine composition of the solution, (Shijiazhuang Yiling Pharmaceutical Co., Ltd., batch number: B1509001); chromatographically pure acetonitrile, methanol (Adamas Reagent Co., Shanghai); analytical pure reagents (Beijing Chemical Works).

2. Extraction and Separation

This may include: (i) adsorbing 5 kg the total extract of the Chinese traditional medicine composition by macroporous resin AB-8™, eluting with 150 L water, 87.5 L 10% ethanol, 225 L 30% ethanol and 250 L 50% ethanol in sequence, and concentrating to obtain extract of each part;

(2) taking 200 g the 50% ethanol elution part extract obtained in the step (i), adding 200 g reversed-phase silica gel ODS-AQ-HG™ S-50 μm to mix sample, naturally airing the mixed sample ODS, loading the sample, and separating by using a reversed-phase ODS-AQ-HG™ S-50 μm open column, wherein the sample height ratio is 1:4; eluting with 6 L methanol-water in a volume ratio of 20:80, 7 L in a volume ratio 40:60, 7 L in a volume ratio 60:40, 5 L in a volume ratio 80:20 and 3 L 100% methanol in sequence under reduced pressure to obtain Fr.A-Fr.E;

(3) taking 50.0 g Fr.A sample obtained in step (2), adding 50.0 g reverse-phase silica gel ODS-AQ-HG™ S-50 μm to mix sample, naturally airing the mixed sample ODS, adding the mixed sample ODS into a sample loading column, separating liquid phase prepared by an upper medium-pressure, wherein a separating column filler was reversed-phase silica gel ODS-AQ-HG™ S-50 μm, gradiently separating liquid phase prepared by medium-pressure, wherein the volume ratio of methanol to water is 25:75-60:40, and the flow rate is 25 mL/min, receiving the fractions in equal volume of 500 mL in a conical flask, concentrating under reduced pressure, identifying the combined fractions through a thin layer chromatography plate, and concentrating under reduced pressure again to obtain Fr.A-1-Fr.A-7;

(4) mixing 3.2 g Fr.A-2 sample obtained in the step (3) with 6.4 g silica gel of 200-300 mesh, loading onto a silica gel column, wherein the sample height ratio was 1:50, carrying out isocratic separation by using a dichloromethane-methanol volume ratio of 8:1, receiving fractions in equal volume of 50 mL, eluting with a volume of 800 mL, and identifying the combined fractions through thin-layer chromatography plate to obtain Fr.A-2-1-Fr.A-2-4;

(5) dissolving the Fr.A-2-2 sample obtained in the step (4) with methanol, the solution was filtered through a 0.45 μm microporous membrane, adopting high performance liquid chromatography, wherein the volume ratio of methanol to water in the mobile phase was 50:50, the flow rate was 12 mL/min, and detection wavelength was 210 nm, to perform primary separation and respectively collecting chromatographic peaks with retention times of 6-8 min, 9-10 min and 12-13 min, recovering the solvent under reduced pressure, and respectively performing the following separation:

a chromatographic peak of 6-8 min, further purified by high performance liquid chromatography, wherein the volume ratio of acetonitrile to water in the mobile phase was 25:75, the flow rate was 12 mL/min, and the detection wavelength was 210 nm, chromatographic column: liquid chromatographic column YMC-Pack R&D ODS-ATM, 250×20 mm, S-10 μm, under these conditions, collecting the chromatographic peak with retention times of 8-9 min, recovering the solvent under decompression to obtained compound 2: aloe-emodin-8-O-β-D-glucopyranoside;

a chromatographic peak of 9-10 min, further purified by high performance liquid chromatography, wherein the volume ratio of methanol to water in the mobile phase was 45:55, the flow rate was 12 mL/min, and the detection wavelength was 210 nm, chromatographic column: liquid chromatographic column YMC-Pack R&D ODS-ATM, 250×20 mm, S-10 µm, under these conditions, collecting the chromatographic peak with retention times of 21-23 min, recovering the solvent under decompression to obtained compound 3: quercitrin;

a chromatographic peak of 12-13 min, further purified by high performance liquid chromatography, wherein acetonitrile to water in the mobile phase was 25:75, the flow rate was 12 mL/min, and the detection wavelength was 210 nm, chromatographic column: liquid chromatographic column YMC-Pack R&D ODS-A™, 250×20 mm, S-10 µm, under these conditions, collecting the chromatographic peak with retention times of 9-10 min, recovering the solvent under decompression to obtained compound 4: matairesinol-4'-O-glucoside;

(6) dissolving the Fr.A-2-3 sample obtained in the step (4) with methanol, the solution was filtered through a 0.45 µm microporous membrane, adopting high performance liquid chromatography, wherein the volume ratio of methanol to water in the mobile phase was 30:70, the flow rate was 12 mL/min, and detection wavelength was 210 nm, to perform primary separation and respectively collecting chromatographic peaks with retention times of 10-11 min, 17-19 min and 21-24 min, recovering the solvent under reduced pressure, chromatographic peaks of 17-19 min is for compound 6: epi-vogeloside, chromatographic peaks of 21-24 min is for compound 7: vogeloside, a chromatographic peak of 10-11 min, further purified by high performance liquid chromatography, wherein the volume ratio of acetonitrile to water in the mobile phase was 15:85, the flow rate was 12 mL/min, and the detection wavelength was 210 nm, chromatographic column: liquid chromatographic column YMC-Pack R&D ODS-ATM, 250×20 mm, S-10 µm, under these conditions, collecting the chromatographic peak with retention times of 14-16 min, recovering the solvent under decompression to obtained compound 5: liquiritin apioside; and (7) dissolving the Fr.A-2-3 sample obtained in the step (3) with methanol, the solution was filtered through a 0.45 µm microporous membrane, adopting high performance liquid chromatography, wherein the volume ratio of methanol to water in the mobile phase was 60:40, the flow rate was 12 mL/min, and detection wavelength was 210 nm, to perform primary separation and respectively collecting chromatographic peaks with retention times of 14-15 min and 19-21 min, and recovering the solvent under reduced pressure, separating out a white precipitate in a dichloromethane-methanol solution with volume ratio of 2:1 from a collecting liquid of chromatographic peak of 19-21 min to obtain compound 8; a chromatographic peak of 14-15 min, further purified by high performance liquid chromatography, wherein the volume ratio of acetonitrile to water in the mobile phase was 30:70, the flow rate was 12 mL/min, and the detection wavelength was 210 nm, chromatographic column: liquid chromatographic column YMC-Pack R&D ODS-ATM, 250×20 mm, S-10 µm, under these conditions, collecting the chromatographic peak with retention times of 18-20 min, recovering the solvent under decompression to obtained compound 1: 10-O-(p-hydroxycinnamoyl)-adoxosidic acid.

3. Structure Identification
3.1 Structure identification of compound 1.

Compound 1: light yellow powder, UV $\lambda_{max}$ (MeOH): 228, 312 nm. Infrared showed hydroxyl (3330 cm$^{-1}$), α, β-unsaturated carbonyl (1680, 1630 cm$^{-1}$) and benzene ring (1603, 1514 cm$^{-1}$). HR-ESI-MS m/z: 521.1699 [M−H]$^{-}$ (calculated value: 521.1659), in combination with NMR data, the molecular formula of the compound was determined to be $C_{25}H_{30}O_{12}$. Unsaturation degree is 11.

$^{1}$H-NMR (DMSO-d$_{6}$, 600 MHz) spectrum (Table 1) showed that the compound contained a pair of trans double bonds δ7.56 (1H, d, J=16.2 Hz), 6.39 (1H, d, J=16.2 Hz) and AB system aromatic hydrogens δ7.55 (2H, d, J=8.4 Hz), 6.79 (2H, d, J=8.4 Hz), chemical shift of hydrogen spectrum was 4.52 (1H, d, J=7.8 Hz), presumed to be the terminal hydrogen of sugar.

$^{13}$C-NMR (DMSO-d$_{6}$, 150 MHz) spectrum (Table 1) showed that the compound contained two conjugated carbonyl carbons ($\delta_C$: 168.4, 167.2) and two distinct fragments, $\delta_C$: 116.2 (2C), 130.8 (2C), 160.2 should be para-hydroxyphenyl fragments, $\delta_C$: 99.3, 77.6, 77.1, 73.6, 70.4, 61.6 is a glucosyl group fragment.

By HMBC, double bonds $\delta_H$ 7.56, 6.39 are related to phenyl carbon $\delta_C$ 125.5, double bonds $\delta_H$ 6.39 and —CH$_2$- $\delta_H$ 4.12 are related to carbonyl group $\delta_C$ 167.2, and the above fragments are not related to other C and H chemical shifts, and the fragments are presumed to be independent fragments of p-hydroxycinnamoyl, and the remaining part of the sugar-free fragment is presumed to be the core. The unsaturation of the parent nucleus is calculated to be 4 (containing a carbonyl group and a double bond), suggesting that the parent nucleus is a double-ring structure. Through the assignment and connection of HSQC and HMBC, it is speculated that the compound is an iridoid, and the parent nucleus of the compound is determined to be adoxosidic acid through literature search.

The remaining fragment was known to be p-hydroxycinnamic acid, esterified to the 10-position of the parent core adoxosidic acid. The compound was identified as a new compound (the configuration of which was not yet confirmed in this experiment and will be confirmed in subsequent studies) as 10-O-(p-hydroxycinnamoye-adoxosidic acid by searching the SciFinder and Reaxys databases.

NMR data of compound 1

TABLE 1

| Carbon site | $\delta_H$ | $\delta_C$ |
| --- | --- | --- |
| 1 | 5.14 (1H, d, J = 6.6 Hz) | 96.5 |
| 3 | 7.40 (1H, s) | 151.6 |
| 4 | | 111.4 |
| 5 | 2.77 (1H, m) | 35.1 |
| 6 | 1.42 (1H, m), 2.09 (1H, m) | 32.1 |
| 7 | 1.35 (1H, m), 1.79 (1H, m) | 27.6 |
| 8 | 2.25 (1H, m) | 40.2 |
| 9 | 1.92 (1H, m) | 43.1 |
| 10 | 4.12 (2H, m) | 67.1 |
| 11 | | 168.4 |
| 1' | 4.52 (1H, d, J = 7.8 Hz) | 99.3 |
| 2' | 3.01 (1H, m) | 73.6 |
| 3' | 3.17 (1H, m) | 77.1$^a$ |
| 4' | 3.14 (1H, m) | 70.4 |
| 5' | 3.17 (1H, m) | 77.6$^a$ |
| 6' | 3.43 (1H, d, J = 11.4 Hz), 3.68 (1H, d, J = 11.4 Hz) | 61.6 |
| 1" | | 125.5 |
| 2"6" | 7.55 (2H, d, J = 8.4 Hz) | 130.8 |
| 3"5" | 6.79 (2H, d, J = 8.4 Hz) | 116.2 |
| 4" | | 160.2 |
| 7" | 7.56 (1H, d, J = 16.2 Hz) | 145.2 |

TABLE 1-continued

| Carbon site | $\delta_H$ | $\delta_C$ |
|---|---|---|
| 8″ | 6.39 (1H, d, J = 16.2 Hz) | 114.5 |
| 9″ |  | 167.2 |

[a]Chemical shifts may need to be exchanged

Figure 2:
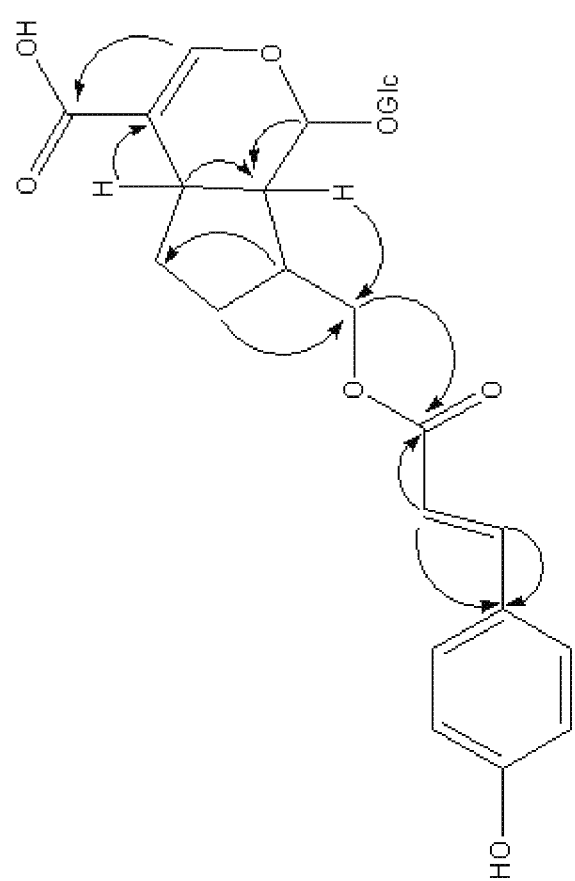
FIG. 2 is a diagram illustrating 1H-detected heteronuclear multiple-bond correlation of the embodiment compound of FIG. 1.

FIG. 1 illustrates a molecular structure of an embodiment compound 1. FIG. 2 illustrates 1H-detected heteronuclear multiple-bond correlation of the compound 1.

3.2 Structure Identification of Known Compounds

Compound 2: yellow powder, ESI-MS m/z: 431 [M−H]−, in combination with NMR data, the molecular formula of the compound was determined to be $C_{21}H_{20}O_{10}$. $^1$H-NMR (DMSO-d$_6$, 600 MHz) $\delta_H$: 12.88 (1H, s, OH), 7.89 (1H, dd, J=1.2, 8.4 Hz, H-5), 7.86 (1H, t, J=7.8 Hz, H-6), 7.72 (1H, dd, J=1.2, 8.4 Hz, H-7), 7.66 (1H, brs, H-4), 7.28 (1H, brs, H-2), 5.17 (1H, d, J=7.8 Hz, anomeric-H), 4.62 (2H, s, CH$_2$OH), 3.72~3.23 (Glc-H)-. $^{13}$C-NMR (DMSO-d$_6$, 150 MHz) $\delta_H$: 188.8 (C-9), 182.6 (C-10), 162.2 (C-1), 158.7 (C-8), 152.7 (C-3), 136.4 (C-6), 135.3 (C-10a), 132.7 (C-4a), 122.9 (C-7), 121.2 (C-2), 121.0 (C-5), 116.4 (C-8a, C-9a), 100.9 (C-1'), 77.7 (C-5'), 77.0 (C-3'), 73.7 (C-2'), 70.0 (C-4'), 62.5 (CH$_2$OH), 61.0 (C-6')—. The characteristics of hydrogen spectrum and data of carbon spectrum above were consistent with what reported in the literature, and the compound was identified as aloe-emodin-8-O-β-D-glucopyranoside.

Compound 3: yellow powder, ESI-MS m/z: 447 [M−H]−, in combination with NMR data, the molecular formula of the compound was determined to be $C_{21}H_{20}O_{11}$. $^1$H-NMR (DMSO-d$_6$, 600 MHz) $\delta_H$: 12.66 (1H, s, 5-OH), 7.31 (1H, d, J=2.4 Hz, H-2'), 7.26 (1H, d, J=2.4, 8.4 Hz, H-6'), 6.87 (1H, d, J=8.4 Hz, H-5'), 6.39 (1H, d, J=2.4 Hz, H-8), 6.21 (1H, d, J=2.4 Hz, H-6), 5.26 (1H, d, J=1.8 Hz, anomeric-H), 0.82 (3H, d, J=6.0 Hz, CH$_3$)—. $^{13}$C-NMR (DMSO-d$_6$, 150 MHz) $\delta_C$: 178.2 (C-4), 164.6 (C-7), 161.7 (C-5), 157.7 (C-2), 156.9 (C-9), 148.9 (C-4'), 145.6 (C-3'), 134.7 (C-3), 1210.5 (C-6'), 121.2 (C-1'), 116.1 (C-5'), 115.9 (C-2'), 104.5 (C-10), 102.3 (C-1″), 99.1 (C-6), 94.1 (C-8), 71.6 (C-4″), 71.0 (C-3″), 70.8 (C-2″), 70.5 (C-5″), 17.9 (C-6″)-. The characteristics of hydrogen spectrum and data of carbon spectrum above were consistent with what reported in the literature, and the compound was identified as quercitrin.

Compound 4: yellow powder, ESI-MS m/z: 519 [M−H]−, in combination with NMR data, the molecular formula of the compound was determined to be $C_{26}H_{32}O_{11}$. $^1$H-NMR (DMSO-d$_6$, 600 MHz) $\delta_H$: 6.99 (1H, d, J=8.4 Hz, H-5), 6.78 (1H, d, J=1.8 Hz, H-2'), 6.67 (2H, m, H-5, H-6'), 6.63 (1H, s, H-2), 6.50 (1H, dd, J=1.8, 8.4 Hz, H-6), 4.84 (1H, d, J=7.8 Hz, H-1″), 4.09 (1H, t, J=7.8 Hz, H-9a), 3.86 (1H, t, J=8.4 Hz, H-9b) 3.72 (6H, d, J=2.4 Hz, 2×OCH$_3$)—. $^{13}$C-NMR (DMSO-d$_6$, 150 MHz) 3c: 178.9 (C-9'), 149.1 (C-3'), 147.9 (C-3), 145.7 (C-4'), 145.4 (C-4), 132.2 (C-1'), 130.0 (C-1), 121.8 (C-6'), 121.2 (C-6), 115.9 (C-5'), 115.6 (C-5), 114.3 (C-2'), 113.1 (C-2), 100.6 (C-1″), 77.4 (C-5″), 77.3 (C-3″), 73.7 (C-2″), 71.1 (C-9), 70.1 (C-4″), 61.1 (C-6″), 56.1 (OCH$_3$), 56.0 (OCH$_3$), 46.0 (C-8'), 41.3 (C-8), 37.3 (C-7), 33.9 (C-7')-. The data of carbon spectrum above were consistent with what reported in the literature, and the compound was identified as matairesinol-4'-O-glucoside.

Compound 5: white powder, ESI-MS m/z: 549 [M−H]−, in combination with NMR data, the molecular formula of the compound was determined to be $C_{26}H_{30}O_{13}$. $^1$-NMR (CD$_3$OD, 600 MHz) $\delta_H$: 7.70 (1H, d, J=9.0 Hz, H-5), 7.40 (2H, d, J=8.4 Hz, H-2', 6'), 7.09 (2H, d, J=9.0 Hz, H-3', 5'), 6.48 (1H, dd, J=2.4, 9.0 Hz, H-6), 6.34 (1H, d, J=2.4 Hz, H-8), 5.46 (1H, d, J=1.2 Hz, H-1‴), 5.39 (1H, dd, J=2.4, 13.2 Hz, H-2), 4.98 (1H, d, J=7.2 Hz, H-1″), 4.04 (1H, d, J=9.6 Hz, H-5‴a), 3.89 (1H, d, J=1.2 Hz, H-2‴), 3.88 (1H, dd, J=1.2, 12.0 HZ, H-6″a), 3.79 (1H, d, J=9.6 Hz, H-5‴b), 2.99 (1H, m, H-3a), 2.74 (1H, dd, J=2.4, 16.8 Hz, H-3b). $^{13}$C-NMR (CD$_3$OD, 150 MHz) $\delta_C$: 193.2 (C-4), 166.7 (C-7), 165.3 (C-8a), 159.0 (C-4'), 134.3 (C-1'), 129.9 (C-5), 128.8 (C-2', 6'), 117.6 (C-3', 5'), 114.9 (C-4a), 111.8 (C-6), 110.7 (C-1″), 103.8 (C-8), 100.7 (C-1‴), 80.7 (C-2), 80.6 (C-3‴), 78.8 (C-5″), 78.6 (C-2″), 78.0 (C-2‴), 77.9 (C-3″), 75.4 (C-4‴), 71.4 (C-4″), 66.0 (C-5″), 62.4 (C-6″), 44.9 (C-3)-. The characteristics of hydrogen spectrum and data of carbon spectrum above were consistent with what reported in the literature, and the compound was identified as liquiritin apioside.

Compound 6: white powder, ESI-MS m/z: 387 [M−H]−, in combination with NMR data, the molecular formula of the compound was determined to be $C_{17}H_{24}O_{10}$. $^1$-NMR (CD$_3$OD, 600 MHz) $\delta_H$: 7.60 (1H, d, J=2.4 Hz, H-3), 5.55 (1H, d, J=1.8 Hz, H-1), 5.48 (1H, m, H-8), 5.31 (1H, s, H-7), 5.29 (1H, m, H-10a), 5.25 (1H, m, H-10b), 4.67 (1H, d, J=7.8 Hz, H-1'), 3.50 (1H, s, 7-OCH$_3$), 3.18 (1H, m, H-5), 2.63 (1H, m, H-9), 1.85 (1H, dd, J=6.0, 13.2 Hz, H-6a), 1.69 (1H, td, J=3.0, 13.8 Hz, H-6b)-. $^{13}$C-NMR (CD$_3$OD, 150 MHz) $\delta_C$: 167.4 (C-11), 154.4 (C-4), 133.3 (C-8), 121.0 (C-10), 105.3 (C-4), 103.3 (C-7), 100.3 (C-1'), 98.5 (C-1), 78.3 (C-5'), 78.0 (C-3'), 74.6 (C-2'), 71.4 (C-4'), 62.6 (C-6'), 57.0 (7-OCH$_3$), 43.5 (C-9), 30.2 (C-6), 22.8 (C-5)-. The characteristics of hydrogen spectrum and data of carbon spectrum above were consistent with what reported in the literature, and the compound was identified as epi-vogeloside.

Compound 7: white powder, ESI-MS m/z: 387 [M−H]−, in combination with NMR data, the molecular formula of the compound was determined to be $C_{17}H_{24}O_{10}$. $^1$H-NMR (CD$_3$OD, 600 MHz) $\delta_H$: 7.58 (1H, d, J=2.4 Hz, H-3), 5.55 (1H, d, J=1.2 Hz, H-1), 5.47 (1H, m, H-8), 5.31 (1H, s, H-7), 5.29 (1H, m, H-10a), 5.26 (1H, m, H-10b), 4.66 (1H, d, J=7.8 Hz, H-1'), 3.54 (1H, s, 7-OCH$_3$), 3.16 (1H, m, H-5), 2.67 (1H, m, H-9), 1.97 (1H, m, H-6a), 1.44 (1H, m, H-6b)-. $^{13}$C-NMR (CD$_3$OD, 150 MHz) $\delta_C$: 167.6 (C-11), 154.1 (C-4), 133.0 (C-8), 121.1 (C-10), 15.4 (C-4), 105.1 (C-7), 99.7 (C-1'), 97.9 (C-1), 78.4 (C-5'), 77.8 (C-3'), 74.7 (C-2'), 71.5 (C-4'), 62.6 (C-6'), 57.1 (7-OCH$_3$), 43.7 (C-9), 31.7 (C-6), 25.3 (C-5)-. The characteristics of hydrogen spectrum were consistent with what reported in the literature carbon, the carbon signal is assigned, and the compound was identified as vogeloside.

Compound 8: white powder, ESI-MS m/z: 209 [M+H]+, in combination with NMR data, the molecular formula of the compound was determined to be $C_{11}H_{12}O_4$. $^1$H-NMR (DMSO-d$_6$, 600 MHz) $\delta_H$: 7.46 (1H, d, J=15.9 Hz, H-7), 7.04 (1H, brs, H-2), 6.99 (1H, d, J=8.1 Hz, H-6), 6.75 (1H, d, J=8.1 Hz, H-5), 6.24 (1H, d, J=15.9 Hz, H-8), 4.15 (2H, q, J=7.1 Hz, H-10), 1.24 (3H, t, J=7.1 Hz, H-11)-. $^{13}$C-NMR (DMSO-d$_6$, 150 MHz) $\delta_C$: 166.5 (C-9), 148.6 (C-4), 145.0 (C-7), 145.6 (C-3), 121.3 (C-6), 125.3 (C-1), 115.7 (C-5), 114.7 (C-2), 113.9 (C-8), 59.6 (C-10), 14.3 (C-11). The characteristics of hydrogen spectrum and data of carbon spectrum above were consistent with what reported in the with a literature, and the compound was identified as ethyl caffeate.

Example 2

An embodiment method may include weighing in proportion: 30 kg fructus Forsythiae, 20 kg honeysuckle, 30 kg isatis root, 6 kg *Rheum officinale,* 10 kg *Pogostemon cablin,* 20 kg *Rhizoma dryopteris* crassirhizomatis, 6 kg *Rhodiola rosea,* 0.5 kg menthol, 10 kg ephedra, 6 kg semen *Armeniacae amarum,* 30 kg *Houttuyni acordata,* 6 kg liquorice and 30 kg *Gypsum fibrosum,* and extracting according to the following processes:

(1) weighing the Chinese traditional medicinal materials according to the weight ratio of the raw material medicines, cleaning and selecting, and crushing as appropriate;

(2) crushing *Pogostemon cablin,* adding 10 times of water to extract volatile oil, extracting for 8 hours, and collecting the volatile oil for later use; after filtering the extracting solution, discarding the residue, and taking the filtrate for later use;

3) extracting fructus Forsythiae, ephedra, *Houttuyni acordata* and *Rheum officinale* three times with 12 times of 70% ethanol for 2.5 hours each time, combining and filtering the extracting solutions, recovering ethanol, and taking the filtrate for later use;

(4) honeysuckle, *Gypsum fibrosum,* isatis root, *Rhizoma dryopteris* crassirhizomatis, liquorice and *Rhodiola rosea,* adding 12 times of water for decocting to boil, adding semen *Armeniacae amarum,* decocting twice for 1 hour each time, combining and filtering the extracting solutions, combining the obtained filtrate with the filtrate after *Pogostemon cablin* oil extraction in the step (2), concentrating to a clear paste with a relative density of 1.10 measured at 60° C., adding ethanol to adjust the alcohol concentration to 70%, and refrigerating and standing; filtering and recovering ethanol until no alcohol smell exists to obtain clear paste for later use; and (5) combining the clear paste obtained in the step (4) with the alcohol extract obtained in the step (3), concentrating to a clear paste with a relative density of 1.15 measured at 60° C., and drying to obtain the total extract for later use.

An embodiment separation method may comprise the following step.

1. Preparation of instrument and materials. This step is the same as that in Example 1. Please refer to the details in Example 1.

2. Extraction and Separation:

This may include adsorbing the solution total extract 5 kg the Chinese traditional medicine composition by d-101 macroporous resin, eluting with water, 10% ethanol, 30% ethanol and 50% ethanol in sequence, and concentrating to obtain extract of each part; remaining steps were the same as in Example 1.

3. Results identification: this step is the same as that of Example 1, where eight compounds are obtained from the separation, which are identical to those obtained in Example 1.

Example 3

The raw material medicine formula is: 27.8 kg fructus Forsythiae, 29.4 kg honeysuckle, 28.5 kg isatis root, 5.5 kg *Rheum officinale,* 9.5 kg *Pogostemon cablin,* 29 kg *Rhizoma dryopteris* crassirhizomatis, 8.7 kg *Rhodiola rosea,* 0.85 kg menthol, 8.8 kg ephedra, 8 kg semen *Armeniacae amarum,* 28.4 kg *Houttuyni acordata,* 9.5 kg liquorice and 27.7 kg *Gypsum fibrosum,* and extracting according to the following processes:

(1) weighing the Chinese traditional medicinal materials according to the weight ratio of the raw material medicines, cleaning and selecting, and crushing as appropriate;

(2) crushing *Pogostemon cablin,* adding 10 times of water to extract volatile oil, extracting for 8 hours, and collecting the volatile oil for later use; after filtering the extracting solution, discarding the residue, and taking the filtrate for later use;

(3) extracting fructus Forsythiae, ephedra, *Houttuyni acordata* and *Rheum officinale* three times with 12 times of 70% ethanol for 2.5 hours each time, combining and filtering the extracting solutions, recovering ethanol, and taking the filtrate for later use;

(4) honeysuckle, *Gypsum fibrosum,* isatis root, *Rhizoma dryopteris* crassirhizomatis, liquorice and *Rhodiola rosea,* adding 12 times of water for decocting to boil, adding semen *Armeniacae amarum,* decocting twice for 1 hour each time, combining and filtering the extracting solutions, combining the obtained filtrate with the filtrate after *Pogostemon cablin* oil extraction in the step (2), concentrating to a clear paste with a relative density of 1.13 measured at 60° C., adding ethanol to adjust the alcohol concentration to 70%, and refrigerating and standing; filtering and recovering ethanol until no alcohol smell exists to obtain clear paste for later use; and (5) combining the clear paste obtained in the step (4) with the alcohol extract obtained in the step (3), concentrating to a clear paste with a relative density of 1.18 measured at 60° C., and drying to obtain the total extract for later use.

An embodiment separation method may comprise the following step.

1. The preparation of instrument and materials is the same as that in Example 1.

2. Extraction and Separation

This step may include adsorbing the solution total extract 5 kg the Chinese traditional medicine composition by HPD-100 macroporous resin, eluting with water, 10% ethanol, 30% ethanol and 50% ethanol in sequence, and concentrating to obtain extract of each part; remaining steps were the same as in Example 1.

3. Results Identification

The step is the same as that in Example 1, where eight compounds are obtained from the separation, which are identical to those obtained in Example 1.

Although embodiments of the present disclosure have been described in detail, it should be understood that various changes, substitutions and alterations can be made herein without departing from the spirit and scope of the disclosure as defined by the appended claims.

Moreover, the scope of the present disclosure is not intended to be limited to the particular embodiments described here. As one of ordinary skill in the art will readily appreciate from the disclosure of the present disclosure that processes, machines, manufacture, compositions of matter, means, methods, or steps, presently existing or later to be developed, may perform substantially the same function or achieve substantially the same result as the corresponding embodiments described herein. Accordingly, the appended claims are intended to include within their scope such processes, machines, manufacture, compositions of matter, means, methods, or steps.

What is claimed is:

1. A method for separating eight components in a composition, wherein the composition is prepared from raw materials in parts by weight comprising: 200-300 parts of fructus Forsythiae, 60-100 parts of ephedra, 40-60 parts of *Rheum officinale,* 200-300 parts of *Houttuyni acordata,* 200-300 parts of honeysuckle, 200-300 parts of isatis root, 60-100 parts of *Pogostemon cablin,* 200-300 parts of *Rhizoma dryopteris* crassirhizomatis, 60-100 parts of *Rhodiola rosea,* 5-9 parts of menthol, 60-100 parts of semen *Arme-*

*niacae amarum,* 60-100 parts of liquorice and 200-300 parts of *Gypsum fibrosum,* wherein the method comprises following steps of:
  (1) adsorbing total extract of the composition by macroporous resin, eluting with water, 10% ethanol, 30% ethanol and 50% ethanol in sequence, respectively collecting eluent of each part, and concentrating to obtain extract of each part;
  (2) taking the extract of an elution part of the 50% ethanol (50% ethanol elution part extract) obtained in step (1), adding reverse-phase octadecyl-modified silica gel to form a first mixture, air drying the first mixture, loading the first mixture, separating by using a reverse-phase octadecyl-modified silica gel open column, and sequentially eluting by using methanol with methanol-water volume ratios of 20:80, 40:60, 60:40, 80:20 and 100% methanol, and sequentially obtaining Fr.A -Fr.E samples, wherein the reverse-phase octadecyl-modified silica gel has a hydrophobic carbon loading and a hydrophilic surface;
  (3) taking the Fr.A sample obtained in step (2), adding the reverse-phase octadecyl-modified silica gel to form a second mixture, air drying the second mixture, adding the second mixture into a sample loading column, separating by medium pressure preparative liquid chromatography, wherein a volume ratio of methanol to water is 25:75-60:40, and a flow rate is 25 mL/min, receiving fractions, concentrating the fractions under reduced pressure, evaluating each fraction through thin layer chromatography, and concentrating under reduced pressure again to obtain Fr.A-1-Fr.A-7 samples;
  (4) mixing the Fr.A-2 sample obtained in the step (3) with silica gel, loading onto a silica gel column, carrying out isocratic separation by using a dichloromethane-methanol volume ratio of 8:1, receiving fractions, evaluating each fraction through thin-layer chromatography, and obtaining Fr.A-2-1-Fr.A-2-4 samples;
  (5) dissolving the Fr.A-2-2 sample obtained in the step (4) with methanol, adopting high performance liquid chromatography, wherein a volume ratio of methanol to water in a mobile phase is 50:50, a flow rate is 12 mL/min, and a detection wavelength is 210 nm, to perform primary separation, and respectively collecting chromatographic peaks with retention times of 6-8 min, 9-10 min and 12-13 min, recovering the solvent under reduced pressure, and respectively performing following separation:
  the chromatographic peak of 6-8 min, further purified by high performance liquid chromatography, wherein a volume ratio of acetonitrile to water in the mobile phase is 25:75, a flow rate is 12 mL/min, and a detection wavelength is 210 nm, chromatographic column: liquid chromatographic column using octadecyl-modified silica gel with fully-endcapped C18 phase, 250×20 mm, under these conditions, collecting the chromatographic peak with retention times of 8-9 min, recovering the solvent under decompression to obtained a compound 2: aloe-emodin-8-O-β-D-glucopyranoside;
  the chromatographic peak of 9-10 min, further purified by high performance liquid chromatography, wherein a volume ratio of methanol to water in a mobile phase is 45:55, a flow rate is 12 mL/min, and a detection wavelength is 210 nm, chromatographic column: liquid chromatographic column using the octadecyl-modified silica gel with fully-endcapped C18 phase, 250×20 mm, under these conditions, collecting the chromatographic peak with retention times of 21-23 min, recovering the solvent under decompression to obtained a compound 3: quercitrin; and
  the chromatographic peak of 12-13 min, further purified by high performance liquid chromatography, wherein a volume ratio of acetonitrile to water in a mobile phase is 25:75, a flow rate is 12 mL/min, and a detection wavelength is 210 nm, chromatographic column: liquid chromatographic column using the octadecyl-modified silica gel with fully-endcapped C18 phase, 250×20 mm, under these conditions, collecting the chromatographic peak with retention times of 9-10 min, recovering the solvent under decompression to obtained a compound 4: matairesinol-4'-O-glucoside;
  (6) dissolving the Fr.A-2-3 sample obtained in the step (4) with methanol, adopting high performance liquid chromatography, wherein a volume ratio of methanol to water in a mobile phase is 30:70, a flow rate is 12 mL/min, and a detection wavelength is 210 nm, to perform primary separation and respectively collecting chromatographic peaks with retention times of 10-11 min, 17-19 min and 21-24 min, recovering the solvent under reduced pressure, chromatographic peaks at 17-19 min is for a compound 6: epi-vogeloside, chromatographic peaks at 21-24 min is for a compound 7: vogeloside, chromatographic peak of 10-11 min, further purified by high performance liquid chromatography, wherein a volume ratio of acetonitrile to water in a mobile phase is 15:85, a flow rate is 12 mL/min, and a detection wavelength is 210 nm, chromatographic column: liquid chromatographic column using the octadecyl-modified silica gel with fully-endcapped C18 phase, 250×20 mm, under these conditions, collecting the chromatographic peak with retention times of 14-16 min, recovering the solvent under decompression to obtained a compound 5: liquiritin apioside; and
  (7) dissolving the Fr.A-3 sample obtained in the step (3) with methanol, adopting high performance liquid chromatography, wherein a volume ratio of methanol to water in a mobile phase is 60:40, a flow rate is 12 mL/min, and a detection wavelength is 210 nm, to perform primary separation and respectively collecting chromatographic peaks with retention times of 14-15 min and 19-21 min, and recovering the solvent under reduced pressure, separating out a white precipitate in a dichloromethane-methanol solution with volume ratio of 2:1 from a collecting liquid of chromatographic peak of 19-21 min to obtain a compound 8; and
  wherein chromatographic peak of 14-15 min is further purified by high performance liquid chromatography, wherein a volume ratio of acetonitrile to water in a mobile phase is 30:70, a flow rate is 12 mL/min, and a detection wavelength is 210 nm, chromatographic column: liquid chromatographic column using the octadecyl-modified silica gel with fully-endcapped C18 phase, 250×20 mm, under these conditions, collecting the chromatographic peak with retention times of 18-20 min, recovering the solvent under decompression to obtained a compound 1: 10-O-(p-hydroxycinnamoyl)-adoxosidic acid.

2. The method for separating the eight components according to claim 1, wherein the composition is further prepared from following raw materials in parts by weight:
  200 parts of fructus Forsythiae, 300 parts of honeysuckle, 200 parts of isatis root, 40 parts of *Rheum officinale,* 60 parts of *Pogostemon cablin,* 300 parts of *Rhizoma* dryopteris crassirhizomatis, 100 parts of *Rhodiola rosea*, 9 parts of menthol, 60 parts of ephedra, 100 parts of semen *Armeniacae amarum*, 200 parts of *Houttuyni acordata*, 100 parts of liquorice and 200 parts of *Gypsum fibrosum*.

3. The method for separating the eight components according to claim 1, wherein the composition is further prepared from following raw materials in parts by weight:
300 parts of fructus Forsythiae, 200 parts of honeysuckle, 300 parts of isatis root, 60 parts of *Rheum officinale*, 100 parts of *Pogostemon cablin*, 200 parts of *Rhizoma dryopteris* crassirhizomatis, 60 parts of *Rhodiola rosea*, 5 parts of menthol, 100 parts of ephedra, 60 parts of semen *Armeniacae amarum*, 300 parts of *Houttuyni acordata*, 60 parts of liquorice and 300 parts of *Gypsum fibrosum*.

4. The method for separating the eight components according to claim 1, wherein the composition is further prepared from following raw materials in parts by weight:
278 parts of fructus Forsythiae, 294 parts of honeysuckle, 285 parts of isatis root, 55 parts of *Rheum officinale*, 95 parts of *Pogostemon cablin*, 290 parts of *Rhizoma dryopteris* crassirhizomatis, 87 parts of *Rhodiola rosea*, 8.5 parts of menthol, 88 parts of ephedra, 80 parts of semen *Armeniacae amarum*, 284 parts of *Houttuyni acordata*, 95 parts of liquorice and 277 parts of *Gypsum fibrosum*.

5. The method for separating the eight components according to claim 1, wherein the total extract of the composition utilized in step (1) of claim 1 is prepared by following steps of:
(A) weighing materials of the composition according to a weight ratio of the raw materials, cleaning and selecting, and crushing the materials;
(B) crushing *Pogostemon cablin*, adding 10 times of water to extract volatile oil, extracting for 8 hours, and collecting the volatile oil for later use; and after filtering extracting solution, discarding the residue, and taking first filtrate for later use;
(C) extracting fructus Forsythiae, ephedra, *Houttuyni acordata* and *Rheum officinale* three times with 12 times of 70% ethanol for 2.5 hours each time, combining and filtering extracting solutions, recovering ethanol, and taking second filtrate for later use;
(D) honeysuckle, *Gypsum fibrosum*, isatis root, *Rhizoma dryopteris* crassirhizomatis, liquorice and *Rhodiola rosea*, adding 12 times of water for decocting to boil, adding semen *Armeniacae amarum*, decocting twice for 1 hour each time, combining and filtering extracting solutions, combining obtained third filtrate with the first filtrate after *Pogostemon cablin* oil extraction in the step (B), concentrating to a clear paste with a relative density of 1.10-1.15 measured at 60° C., adding ethanol to adjust alcohol concentration to 70%, and refrigerating and standing; filtering and recovering ethanol until no alcohol smell exists to obtain clear paste for later use; and
(E) combining the clear paste obtained in the step (D) with alcohol extract obtained in the step (C), concentrating to a clear paste with a relative density of 1.15-1.20 measured at 60° C., and drying to obtain the total extract for later use.

6. The method for separating the eight components according to claim 1:
(a) step (1) of claim 1 comprising: adsorbing 5 kg the total extract of the composition by macroporous resin, eluting with 150 L water, 87.5 L 10% ethanol, 225 L 30% ethanol and 250 L 50% ethanol in sequence, and concentrating to obtain extract of each part;
(b) step (2) of claim 1 comprising: taking 200 g of the 50% ethanol elution part extract obtained in the step (a), adding 200 g of the reverse-phase octadecyl-modified silica gel to form a third mixture, air drying the third mixture, loading the third mixture, and separating by using the reverse-phase octadecyl-modified silica gel open column, wherein a sample height ratio is 1:4, eluting with 6 L methanol-water in a volume ratio of 20:80, 7 L in a volume ratio 40:60, 7 L in a volume ratio 60:40, 5 L in a volume ratio 80:20 and 3 L 100% methanol in sequence under reduced pressure to obtain the Fr.A-Fr.E samples;
(c) step (3) of claim 1 comprising: taking 50.0 g of the Fr.A sample obtained in step (b), adding 50 g of the reverse-phase octadecyl-modified silica gel to form a fourth mixture, air drying the fourth mixture, adding the fourth mixture into a sample loading column, separating by medium pressure preparative liquid chromatography, wherein a volume ratio of methanol to water is 25:75-60:40, and a flow rate is 25 mL/min, receiving fractions, concentrating the fractions under reduced pressure, evaluating each fraction through thin layer chromatography, and concentrating under reduced pressure again to obtain the Fr.A-1-Fr.A-7 samples;
(d) step (4) of claim 1 comprising: mixing 3.2 g of the Fr.A-2 sample obtained in the step (c) with 6.4 g silica gel of 200-300 mesh, loading onto a silica gel column, wherein a sample height ratio is 1:50, carrying out isocratic separation by using a dichloromethane-methanol volume ratio of 8:1, receiving fractions, evaluating each fraction through thin-layer chromatography, and obtaining the Fr.A-2-1-Fr.A-2-4 samples;
(e) step (5) of claim 1 comprising: dissolving the Fr.A-2-2 sample obtained in the step (d) with methanol to generate a solution, wherein the solution is filtered through a 0.45 μm microporous membrane, adopting high performance liquid chromatography, wherein a volume ratio of methanol to water in a mobile phase is 50:50, a flow rate is 12 mL/min, and a detection wavelength is 210 nm, to perform primary separation and respectively collecting chromatographic peaks with retention times of 6-8 min, 9-10 min and 12-13 min, recovering the solvent under reduced pressure, and respectively performing following separation:
the chromatographic peak of 6-8 min, further purified by high performance liquid chromatography, wherein the volume ratio of acetonitrile to water in the mobile phase is 25:75, the flow rate is 12 mL/min, and the detection wavelength is 210 nm, chromatographic column: liquid chromatographic column using the octadecyl-modified silica gel with fully-endcapped C18 phase, 250×20 mm, under these conditions, collecting the chromatographic peak with retention times of 8-9 min, recovering the solvent under decompression to obtained the compound 2: aloe-emodin-8-O-β-D-glucopyranoside; and
the chromatographic peak of 9-10 min, further purified by high performance liquid chromatography, wherein the volume ratio of methanol to water in the mobile phase is 45:55, the flow rate is 12 mL/min, and the detection wavelength is 210 nm, chromatographic column: liquid chromatographic column using the octadecyl-modified silica gel with fully-endcapped C18 phase, 250×20 mm, under these conditions, collecting the chromatographic peak with retention times of 21-23 min, recovering the solvent under decompression to obtained the compound 3: quercitrin;

the chromatographic peak of 12-13 min, further purified by high performance liquid chromatography, wherein the volume ratio of acetonitrile to water in the mobile phase is 25:75, the flow rate is 12 mL/min, and the detection wavelength is 210 nm, chromatographic column: liquid chromatographic column using the octadecyl-modified silica gel with fully-endcapped C18 phase, 250×20 mm, under these conditions, collecting the chromatographic peak with retention times of 9-10 min, recovering the solvent under decompression to obtained the compound 4: matairesinol-4'-O-glucoside;

(f) step (6) of claim 1 comprising: dissolving the Fr.A-2-3 sample obtained in the step (d) with methanol, the solution is filtered through a 0.45 μm microporous membrane, adopting high performance liquid chromatography, wherein the volume ratio of methanol to water in the mobile phase is 30:70, the flow rate is 12 mL/min, and detection wavelength is 210 nm, to perform primary separation and respectively collecting chromatographic peaks with retention times of 10-11 min, 17-19 min and 21-24 min, recovering the solvent under reduced pressure, the chromatographic peaks of 17-19 min is for the compound 6: epi-vogeloside, the chromatographic peaks of 21-24 min is for the compound 7: vogeloside, the chromatographic peak of 10-11 min, further purified by high performance liquid chromatography, wherein the volume ratio of acetonitrile to water in the mobile phase is 15:85, the flow rate is 12 mL/min, and the detection wavelength is 210 nm, chromatographic column: liquid chromatographic column using the octadecyl-modified silica gel with fully-endcapped C18 phase, 250×20 mm, under these conditions, collecting the chromatographic peak with retention times of 14-16 min, recovering the solvent under decompression to obtained the compound 5: liquiritin apioside; and (g) step (7) of claim 1 comprising: dissolving the Fr.A-3 sample obtained in the step (c) with methanol, the solution is filtered through a 0.45 μm microporous membrane, adopting high performance liquid chromatography, wherein the volume ratio of methanol to water in the mobile phase is 60:40, the flow rate is 12 mL/min, and detection wavelength is 210 nm, to perform primary separation and respectively collecting chromatographic peaks with retention times of 14-15 min and 19-21 min, and recovering the solvent under reduced pressure, separating out a white precipitate in a dichloromethane-methanol solution with volume ratio of 2:1 from a collecting liquid of chromatographic peak of 19-21 min to obtain the compound 8; and wherein the chromatographic peak of 14-15 min is further purified by high performance liquid chromatography, wherein the volume ratio of acetonitrile to water in the mobile phase is 30:70, the flow rate is 12 mL/min, and the detection wavelength is 210 nm, chromatographic column: liquid chromatographic column using the octadecyl-modified silica gel with fully-endcapped C18 phase, 250×20 mm, under these conditions, collecting the chromatographic peak with retention times of 18-20 min, recovering the solvent under decompression to obtained the compound 1: 10-O-(p-hydroxycinnamoyl)-adoxosidic acid.

7. The method for separating the eight components according to claim 6, wherein the composition is further prepared from following raw materials in parts by weight:

200 parts of fructus Forsythiae, 300 parts of honeysuckle, 200 parts of isatis root, 40 parts of *Rheum officinale*, 60 parts of *Pogostemon cablin,* 300 parts of *Rhizoma dryopteris* crassirhizomatis, 100 parts of *Rhodiola rosea,* 9 parts of menthol, 60 parts of ephedra, 100 parts of semen *Armeniacae amarum,* 200 parts of *Houttuyni acordata,* 100 parts of liquorice and 200 parts of *Gypsum fibrosum.*

8. The method for separating the eight components according to claim 6, wherein the composition is further prepared from following raw materials in parts by weight:

300 parts of fructus Forsythiae, 200 parts of honeysuckle, 300 parts of isatis root, 60 parts of *Rheum officinale,* 100 parts of *Pogostemon cablin,* 200 parts of *Rhizoma dryopteris* crassirhizomatis, 60 parts of *Rhodiola rosea,* 5 parts of menthol, 100 parts of ephedra, 60 parts of semen *Armeniacae amarum,* 300 parts of *Houttuyni acordata,* 60 parts of liquorice and 300 parts of *Gypsum fibrosum.*

9. The method for separating the eight components according to claim 6, wherein the composition is further prepared from following raw materials in parts by weight:

278 parts of fructus Forsythiae, 294 parts of honeysuckle, 285 parts of isatis root, 55 parts of *Rheum officinale,* 95 parts of *Pogostemon cablin,* 290 parts of *Rhizoma dryopteris* crassirhizomatis, 87 parts of *Rhodiola rosea,* 8.5 parts of menthol, 88 parts of ephedra, 80 parts of semen *Armeniacae amarum,* 284 parts of *Houttuyni acordata,* 95 parts of liquorice and 277 parts of *Gypsum fibrosum.*

10. The method for separating the eight components according to claim 6, wherein the total extract of the composition utilized in step (a) of claim 6 is prepared by following steps of:

(A) weighing materials of the composition according to a weight ratio of the raw materials, cleaning and selecting, and crushing the materials;

(B) crushing *Pogostemon cablin,* adding 10 times of water to extract volatile oil, extracting for 8 hours, and collecting the volatile oil for later use; and after filtering extracting solution, discarding the residue, and taking first filtrate for later use;

(C) extracting fructus Forsythiae, ephedra, *Houttuyni acordata* and *Rheum officinale* three times with 12 times of 70% ethanol for 2.5 hours each time, combining and filtering extracting solutions, recovering ethanol, and taking second filtrate for later use;

(D) honeysuckle, *Gypsum fibrosum,* isatis root, *Rhizoma dryopteris* crassirhizomatis, liquorice and *Rhodiola rosea,* adding 12 times of water for decocting to boil, adding semen *Armeniacae amarum,* decocting twice for 1 hour each time, combining and filtering extracting solutions, combining obtained third filtrate with the first filtrate after *Pogostemon cablin* oil extraction in the step (B), concentrating to a clear paste with a relative density of 1.10-1.15 measured at 60° C., adding ethanol to adjust alcohol concentration to 70%, and refrigerating and standing; filtering and recovering ethanol until no alcohol smell exists to obtain clear paste for later use; and (E) combining the clear paste obtained in the step (D) with alcohol extract obtained in the step (C), concentrating to a clear paste with a relative density of 1.15-1.20 measured at 60° C., and drying to obtain the total extract for later use.

\* \* \* \* \*